(12) United States Patent
Aho

(10) Patent No.: US 7,998,053 B2
(45) Date of Patent: Aug. 16, 2011

(54) TRANSCRANIAL MAGNETIC STIMULATION INDUCTION COIL DEVICE AND METHOD OF MANUFACTURE

(75) Inventor: Matti Aho, Nummela (FI)

(73) Assignee: Nexstim Oy, Helsinki (FI)

( * ) Notice: Subject to any disclaimer, the term of this patent is extended or adjusted under 35 U.S.C. 154(b) by 1001 days.

(21) Appl. No.: 11/847,511

(22) Filed: Aug. 30, 2007

(65) Prior Publication Data
US 2008/0058581 A1 Mar. 6, 2008

(51) Int. Cl.
*A61N 1/00* (2006.01)

(52) U.S. Cl. ........ 600/13; 600/9; 336/90; 336/210; 336/232

(58) Field of Classification Search ........ 600/9–15; 128/897; 336/90–92, 96, 197, 205, 208, 336/226, 232
See application file for complete search history.

(56) References Cited

U.S. PATENT DOCUMENTS

| | | | | |
|---|---|---|---|---|
| 6,179,770 | B1* | 1/2001 | Mould | 600/13 |
| 6,261,221 | B1* | 7/2001 | Tepper et al. | 600/14 |
| 2005/0182287 | A1* | 8/2005 | Becker | 600/13 |
| 2006/0004244 | A1* | 1/2006 | Phillips et al. | 600/13 |

FOREIGN PATENT DOCUMENTS
WO WO 99/27995 6/1999
* cited by examiner

*Primary Examiner* — Charles A Marmor, II
*Assistant Examiner* — Carrie Dorna
(74) *Attorney, Agent, or Firm* — Seppo Laine Oy; Joshua P. Wert

(57) ABSTRACT

A transcranial magnetic stimulation induction coil device ("TMS coil device") is manufactured to contain coil windings of a predetermined size and shape and fixedly positioned at a predetermined location within and orientation in relation to a casing of the TMS coil device. In one embodiment, the coil windings are encased in a casting at a predetermined location within and orientation in relation to the casting, and the casting is fixedly positioned at a predetermined location within and orientation in relation to the casing. The size and shape of the coil windings and the casing within, and the location and orientation of the coil windings in relation to each other and the casing of, the TMS coil device are known with a high level of precision, such that navigated brain stimulation can be performed with the TMS coil device with a high degree of accuracy. In another embodiment, the TMS coil device defines a space interposed between the coil windings and the casing and containing a gas which absorbs heat energy generated at the coil windings, thereby reducing the rate of transfer of heat energy from the coil windings to the casing during operation of the TMS coil device.

15 Claims, 10 Drawing Sheets

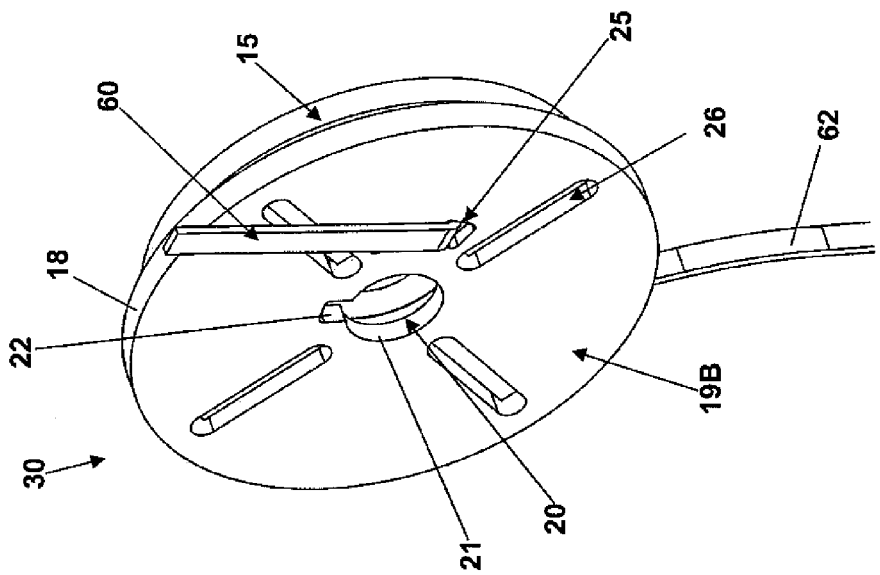
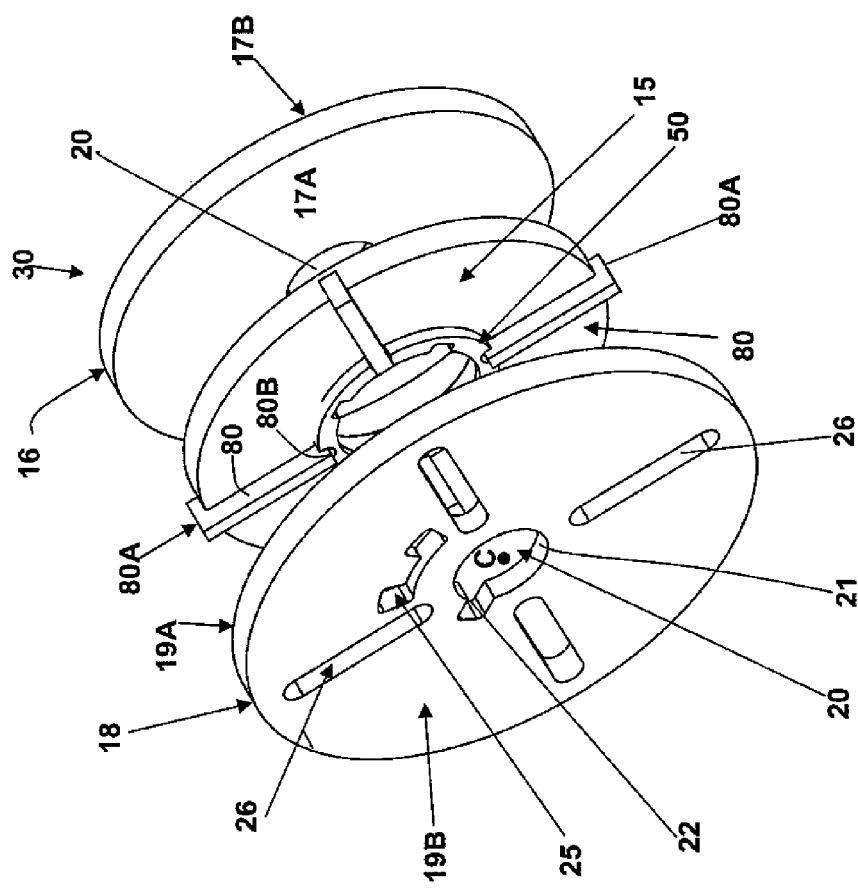
FIG. 2C
FIG. 2B

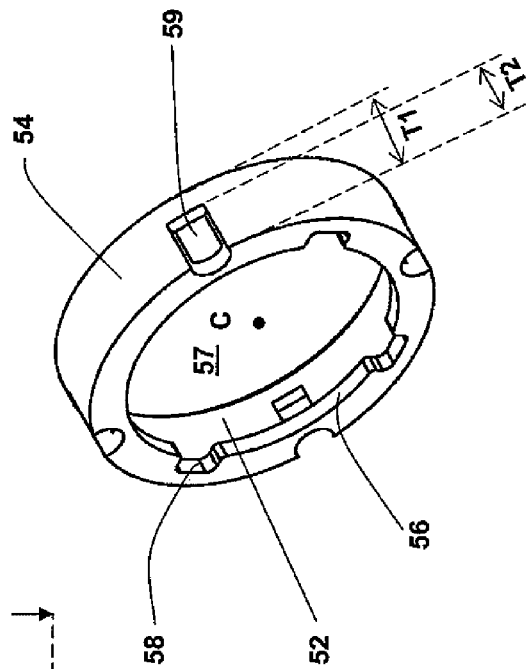
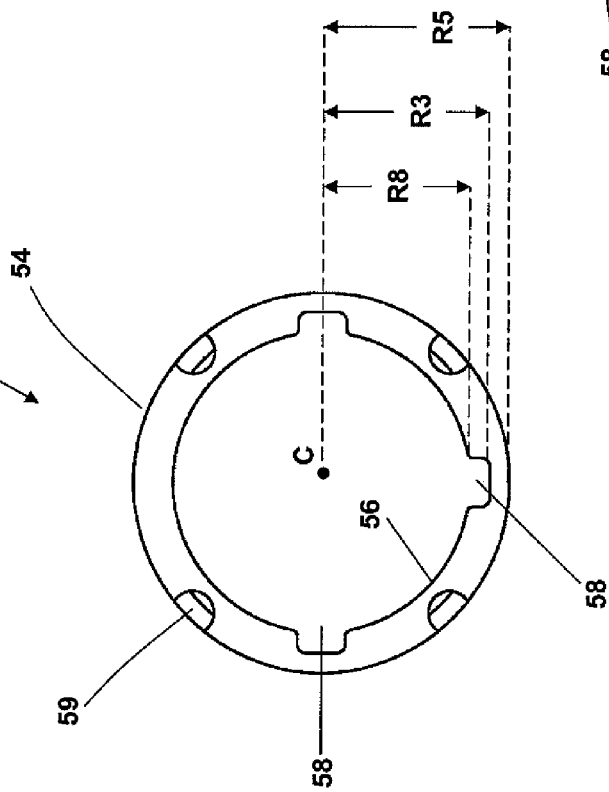

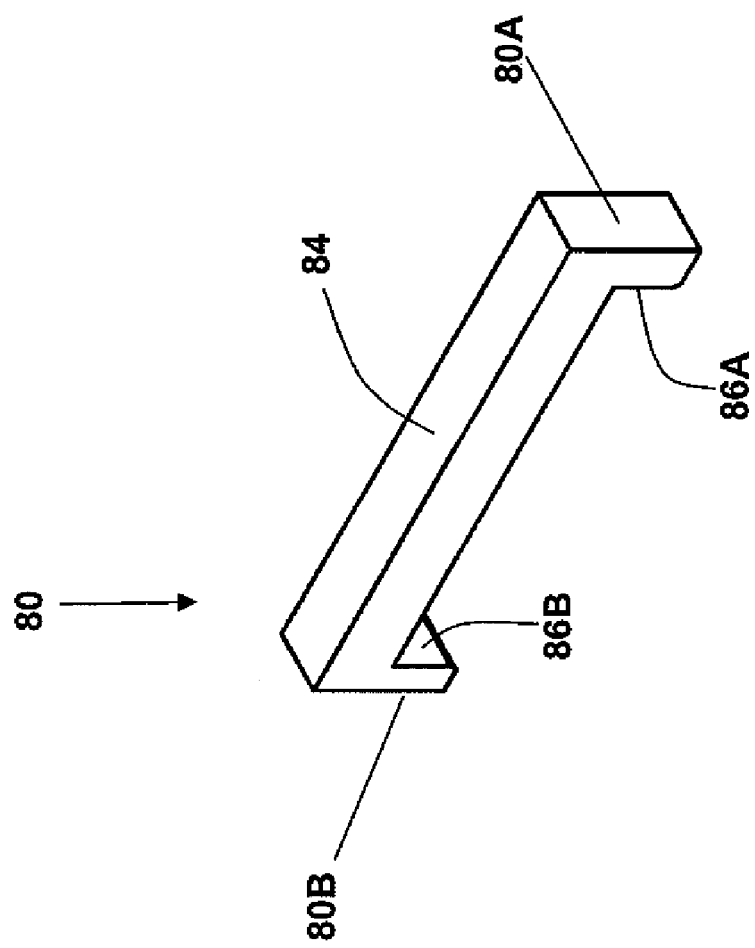

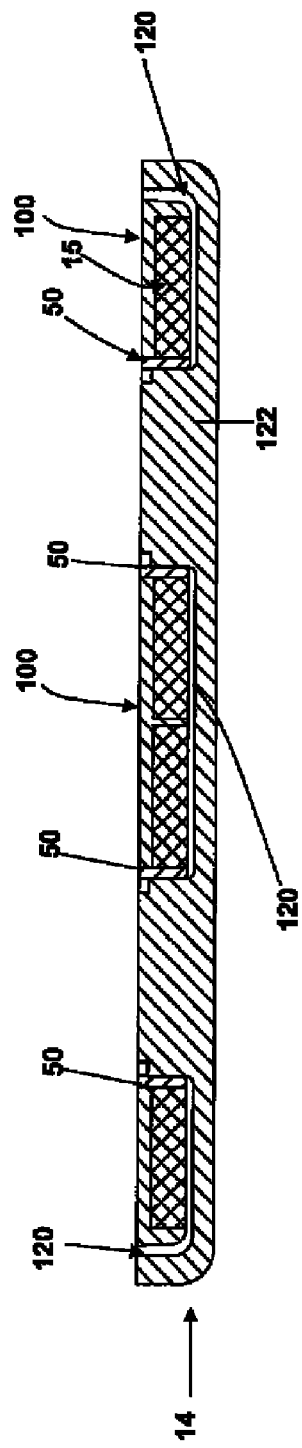
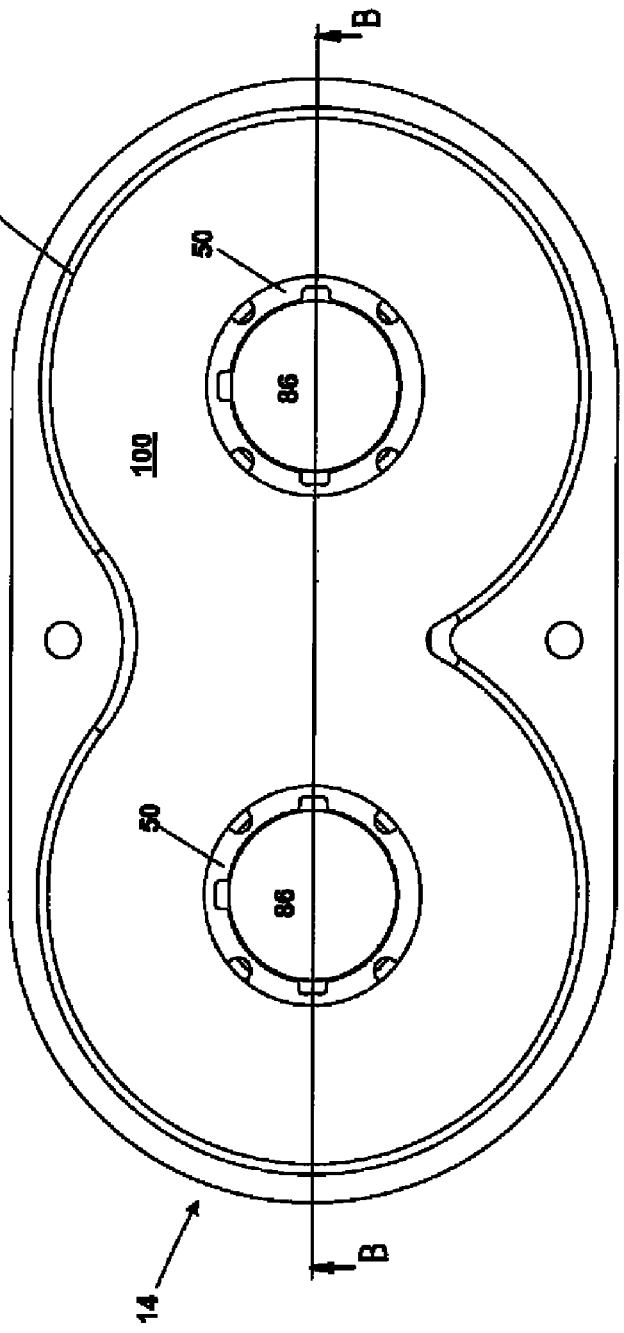
FIG. 5B
FIG. 5A

TRANSCRANIAL MAGNETIC STIMULATION INDUCTION COIL DEVICE AND METHOD OF MANUFACTURE

CROSS REFERENCE TO RELATED APPLICATION

This application claims the benefit of U.S. Provisional Application No. 60/823,991 filed Aug. 30, 2006, assigned to the assignee of this application and incorporated by reference herein.

FIELD OF THE INVENTION

The present invention relates generally to transcranial magnetic stimulation and, more particularly, to a transcranial magnetic stimulation induction coil device that can be navigated with a high level of precision.

BACKGROUND OF THE INVENTION

Transcranial magnetic stimulation ("TMS") uses an induction coil to induce an electric field ("E-field") within the brain. The locations of the brain exposed to a strong enough E-field will become activated, or stimulated. In navigated brain stimulation ("NBS"), the E-field induced in the brain by a TMS induction coil device is graphically represented on a display. As part of NBS, a three-dimensional ("3D") localization system is used to locate the TMS coil device accurately with respect to a subject's head. The localization system correlates TMS coil device location information with anatomical information representative of a subject's brain, which typically is obtained from magnetic resonance imaging ("MRI") of the brain. The E-field information is shown as an overlay on a graphical display of the subject's brain generated from the MRI images of the brain. By viewing the display, the user can interactively position the TMS coil device, in real time, in relation to the brain to stimulate a desired location of the brain.

A TMS induction coil device typically includes coils having 5 to 30 loops (windings) of copper wire located in a casing. The windings are normally circularly shaped or in the form of a FIG. 8. The shape, and the location of the maximum, of the E-field induced in the brain depend on the exact shape of the coil windings within the TMS coil device and their location and orientation with respect to the brain. In NBS, the strength and location of the E-field induced in the brain by the TMS coil device is determined from information representative of the location and orientation of the casing of the TMS coil device in relation to the brain and the location and orientation of the coil windings within and in relation to, respectively, the casing. The location and orientation of the casing is obtained from a navigation or tracking device, such as an infrared tracking device including an infrared transceiver and infrared reflective elements attached to the TMS coil device, that tracks the movement of the casing, as is conventional in the art. The location and orientation of the coil windings within the casing are determined by generating a model of the coil windings within the casing of the TMS coil device using information obtained from, for example, X-ray images of the casing of the TMS coil device.

It is known that, in NBS, navigation accuracy and the accuracy of the determination of the E-field induced in the brain are greatly affected by any inaccuracies in the model of the coil windings within the casing of the TMS coil device. The manufacturer of a TMS coil device provides information on the location and orientation of the coil windings within the casing of a TMS coil device, which the manufacturer typically obtains by X-raying the casing of the TMS coil device, for use in NBS. The location and orientation information provided by the manufacturer corresponds to the location and orientation in the casing at which the coil windings are expected to be positioned during manufacture of the casing.

In presently available TMS coil devices, such as, for example, those sold by MAGSTIM and MEDTRONIC, however, the coil windings are not necessarily at the expected location within or orientation in relation to the casing, as indicated by the supplier of the devices, and in some circumstances, for example, are up to about 10 mm away from the expected location. The difference between the actual and expected locations of the coil windings is attributable to manufacturing tolerances relating to the placement of the coil windings within the casing. Also, the difference exists because, in the prior art, the coil windings ordinarily are positioned relatively freely within the casing of a TMS coil device. Thus, the coil winding location and orientation information provided for current TMS coil devices, which would then be relied upon for NBS, does not correspond with the actual location and orientation of the coil windings within the casing. It has been determined that, where the difference between the expected and actual locations of the coil windings in the casing is up to about 10 mm, inaccuracies in the computation of the location and strength of the E-field can be up to about 10 mm and greater than tenths of a percent, respectively.

In addition, during operation of a TMS coil device, resistive losses in the copper wire from which the coil windings are formed generate a substantial amount of heat energy relatively quickly, especially when the TMS coil device is operated to supply many sequential pulses to the brain. The heat energy generated in the coil windings raises the temperature of the coil windings and also the surrounding casing. Consequently, the temperature of the surface of the casing adjacent or in contact with the head of a subject increases as the heat energy is transferred to the casing. International standards, e.g., IEC-60601-1, require that the temperature of the outer surface of the casing of a TMS coil device should not exceed 41° C., such that the outer surface of the casing remains at a temperature considered to be safe for contact with a subject, such as a human or animal.

Thus, the temperature of the casing outer surface is a limit on the number of times that the TMS coil device can be sequentially pulsed. The current limitations on the number of pulses that can be sequentially applied by a TMS coil device restricts the potential applications of the TMS coil device, and also lengthens the time that a patient undergoing TMS must endure such procedure, which is undesirable.

In prior art TMS coil devices, the convection techniques of having fluid re-circulate about, or at least partially surround, the coil windings have been used to increase the rate of transfer of heat energy away from the coil windings. In addition, the fluid operates to decrease the rate of transfer of heat energy from the coil windings to the casing, and thus, decrease the rate at which the temperature of the casing outer surface increases. Such uses of fluid to increase the heat capacity of the TMS coil device, however, complicate the design and construction of the TMS coil device, which must be made waterproof, and also substantially increase the weight of the casing, which makes the TMS coil device more bulky and difficult to maneuver.

Further, in some prior art TMS coil devices, a reduction in the rate of heat energy transfer from the coil windings to the portion of the casing outer surface that would face or contact the subject's head is achieved because the coil windings are positioned a greater distance away from the casing portion than in other TMS coil devices. The distance of the coil windings from the subject's head, however, impacts the maximum E-field that can be induced in the brain. Therefore, it is disadvantageous for the coil windings to be positioned so far away from the casing outer surface portion that the maximum E-field that can be induced in the brain is undesirably diminished.

Therefore, there exists a need for a TMS coil device that can be manufactured with ease, repeatedly and inexpensively to provide that the coil windings are of a predetermined size and shape and are positioned, with great accuracy, at a predetermined location within and orientation in relation to a casing of the TMS coil device having a predetermined size and shape and, furthermore, to provide that the rate of transfer of heat energy from the coil windings to the casing outer surface is minimized without adversely impacting the maximum E-field that can be induced in the subject's brain.

SUMMARY OF THE INVENTION

In accordance with the present invention, a TMS coil device contains coil windings, preferably made of copper, having a predetermined size and shape and which are substantially precisely positioned at a predetermined location within and orientation in relation to a casing of the TMS coil device, the casing also having a predetermined size and shape.

In one embodiment of the TMS coil device, each of the coil windings in the TMS coil device includes inner and outer diameter surfaces and a fastener extending between and coupled to the inner and outer diameter surfaces, where the fastener preferably is only on one side of the coil winding. The fastener substantially fixes the size and shape of the coil winding.

In another embodiment of the TMS coil device, the coil windings of the TMS coil device, preferably with respective fasteners attached to the inner and outer diameter surfaces, are encased in a casting having a predetermined size and shape and at a predetermined location within and orientation in relation to, respectively, the casting, such that the coil windings are substantially fixed in location and orientation in relation to each other and the casing.

In a further embodiment, a casting having a predetermined size and shape and encasing two coil windings of predetermined size and shape, at a predetermined location within and orientation in relation to the casting, and preferably with respective fasteners attached to the inner and outer diameter surfaces of the coil windings, can be coupled to a casing of a TMS coil device having a predetermined size and shape, such that, when the casting is coupled to the casing, the coil windings are substantially fixed at a predetermined location within and orientation in relation to the casing. In a further embodiment, the casting containing the encased coil windings includes an aperture for mating with a projection of the casing, such that, when the projection of the casing is mated to the aperture of the casting, the coil windings within the casting are substantially fixed at a predetermined location within and orientation in relation to the casing.

In a further embodiment, the casting with the encased coil windings is coupled to and within the casing, such that a space is defined intermediate at least a portion of the casting and a portion of a bottom wall of the casing whose outer surface will be disposed adjacent or in contact with a subject's head during operation of the TMS coil device. The space includes at least one gas, preferably air, which reduces the rate of transfer of heat energy from the coil windings to the bottom wall of the casing.

In another embodiment, the portion of the casing on the side of the coil windings opposite to the bottom wall of the casing contains a phase transition material, which absorbs heat energy when transforming from solid to liquid and has a low conductivity, such as about 0.1-0.2 W/m*K. The low conductivity of the phase transition material reduces the absorption of heat energy from the coil windings into the casing. In one embodiment, the phase transition material is mixed with high conductivity material, such as ceramic, used to form the casing.

BRIEF DESCRIPTION OF THE DRAWINGS

Other objects and advantages of the present invention will be apparent from the following detailed description of the presently preferred embodiments, which description should be considered in conjunction with the accompanying drawings in which like references indicate similar elements and in which:

FIG. 2B is partially exploded, perspective view of the apparatus and the coil winding of FIG. 2A.

FIG. 2C is a perspective view of the apparatus of FIG. 2A at a step during manufacture of the coil winding.

FIGS. 2G and 2H are top and perspective views, respectively, of an exemplary positioning ring of the apparatus of FIG. 2A.

FIG. 2I is a perspective view of a fastener of the apparatus of FIG. 2A.

FIG. 5A is top view of an exemplary casing containing a casting with coil windings, where the wall of the casing is spaced from the coil windings, in accordance with the present invention.

FIG. 5B is a cross-sectional of the casing containing the casting of FIG. 5A taken at line B-B.

DETAILED DESCRIPTION OF THE INVENTION

Figure 1:
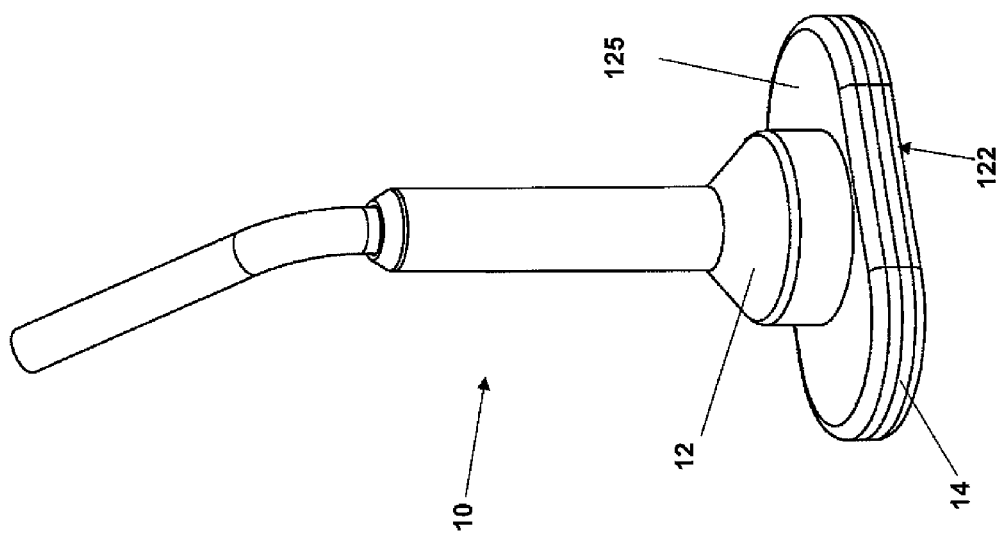
FIG. 1 is a perspective view of an exemplary TMS coil device in accordance with the present invention.
Figure 2A:
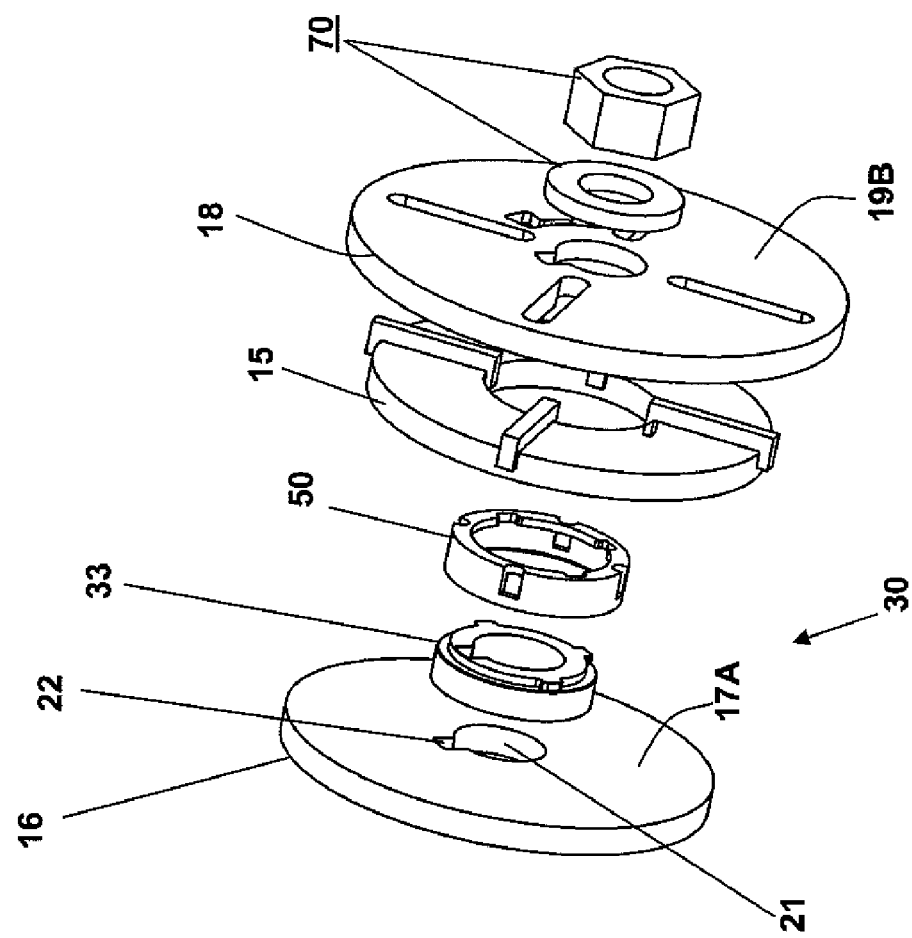
FIG. 2A is an exploded, perspective view of an exemplary apparatus for manufacture of a coil winding for a TMS coil device, with the coil winding as manufactured by the apparatus, in accordance with the present invention.
Figure 2D:
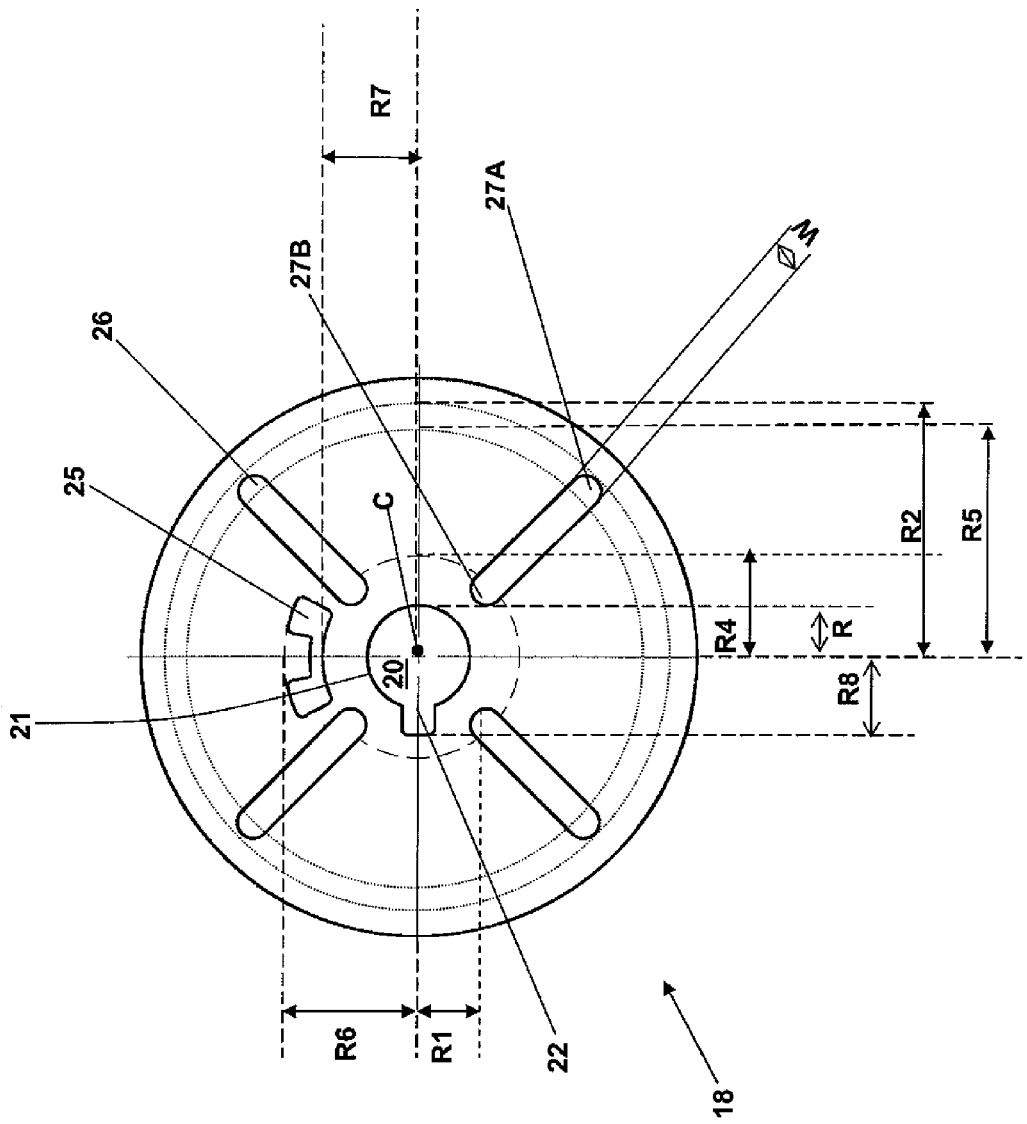
FIG. 2D is a plan view of an exemplary guiding disk of the apparatus of FIG. 2A.
Figure 2E:
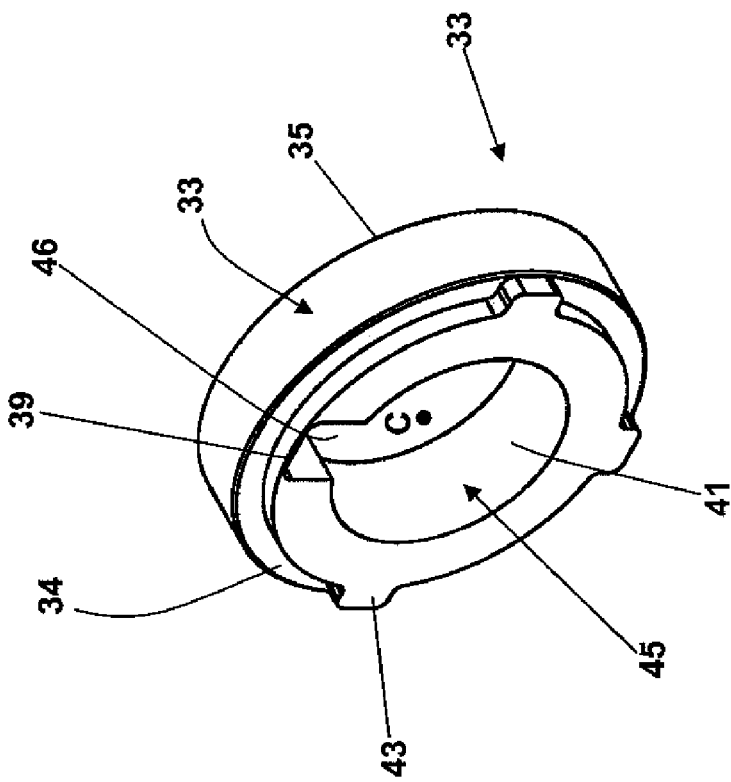
FIGS. 2E and 2F are top and perspective views, respectively, of an exemplary coupling ring of the apparatus of FIG. 2A.
Figure 2F:
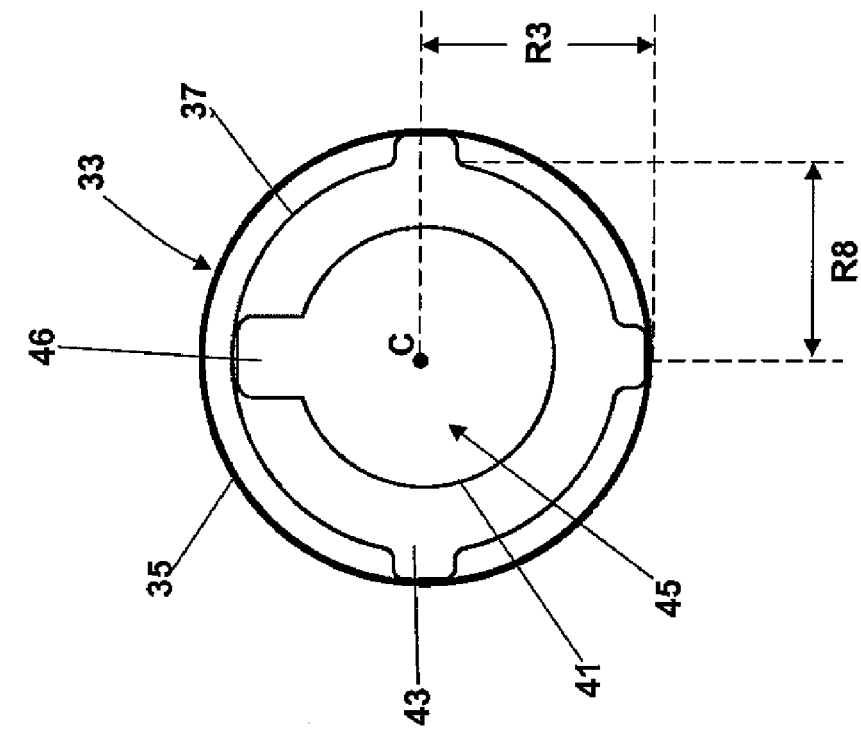
Figure 3:
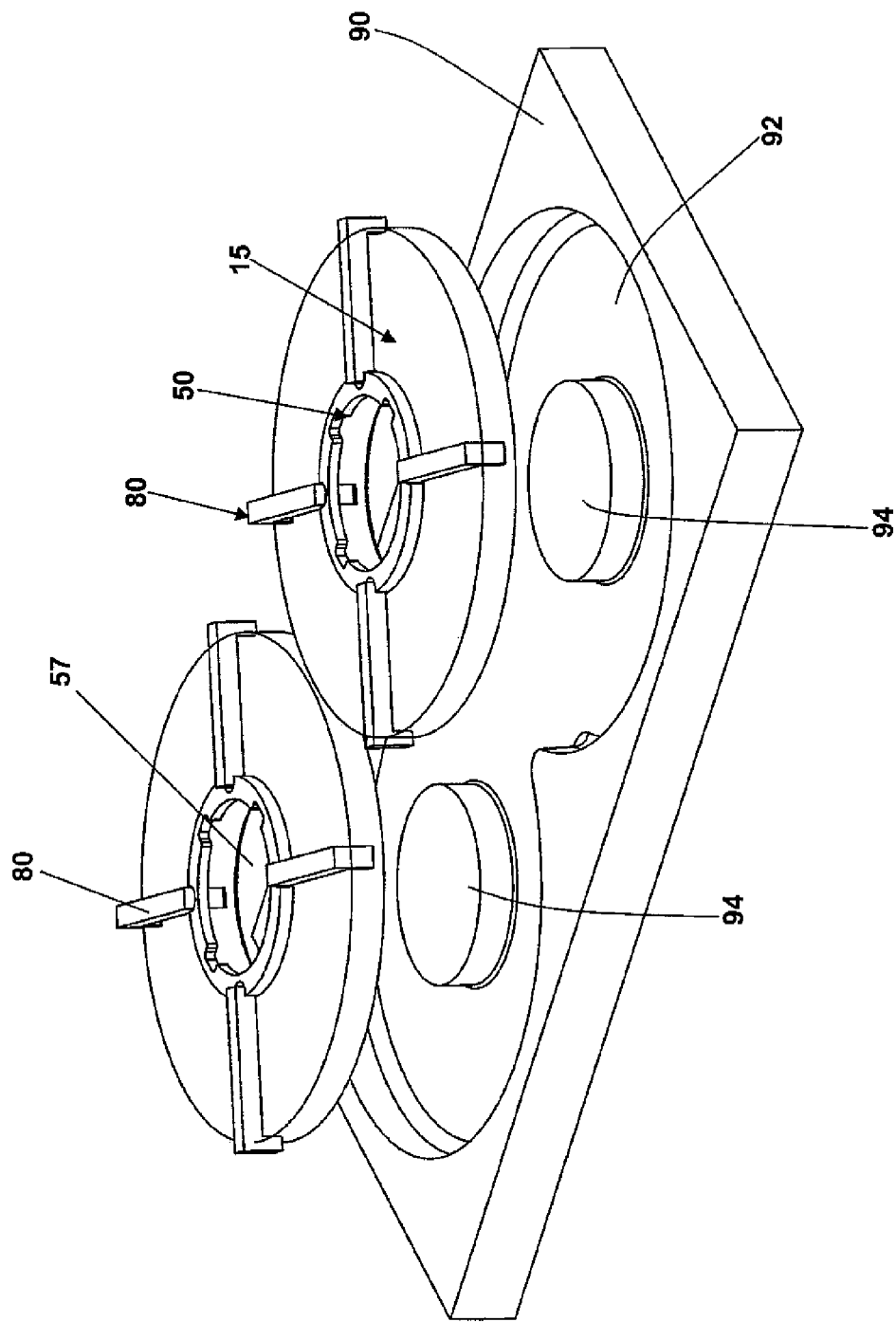
FIG. 3 is a perspective view of exemplary coil windings positioned above a mold for use in manufacture of an exemplary casting containing the coil windings, in accordance with present invention.
Figure 4:
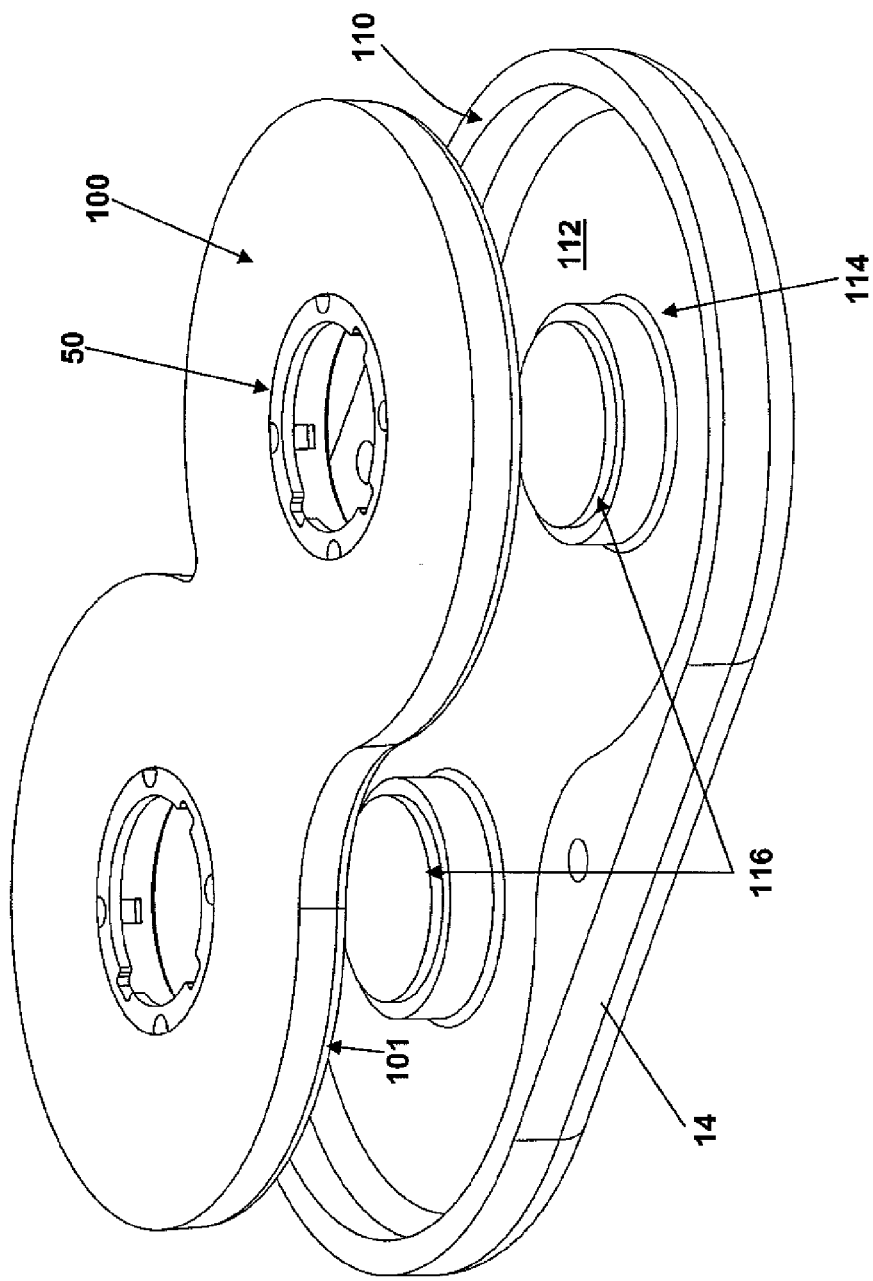
FIG. 4 is a perspective view of an exemplary casting including coil windings positioned above a casing to which the casting can be fixedly coupled, in accordance with the present invention.

FIG. 1 is an exemplary embodiment of a TMS coil device 10, in accordance with the present invention, including a casing 12 containing induction coil windings 15 of predetermined size and shape, an exemplary embodiment of which is described in detail in the text accompanying the discussion of FIGS. 2-4, and substantially fixed, with a high level of precision, at a predetermined location within and orientation in relation to a bottom portion 14 of the casing 12. The casing 12 and an interior region of the bottom portion 14 of the casing 12 have a predetermined size and shape, as discussed in detail below in the text accompanying the discussion of FIGS. 4-5, such that the coil windings 15, when installed within the bottom portion 14 of the casing 15, is substantially precisely fixed at a predetermined location within and orientation in relation to the bottom portion 14 of the casing 12, and thus at a predetermined location and orientation in relation to a bottom outer surface 122 of the bottom portion 14 of the casing 12

FIGS. 2A and 2B illustrate exploded views of an exemplary apparatus 30 for manufacture of the exemplary induction coil winding 15, in accordance with the present invention. Referring to FIGS. 2A and 2B, and also to FIG. 2C, which shows a partial view of the apparatus 30 during an intermediate step in the manufacture of the coil winding 15, the apparatus 30 includes circularly-shaped guidance disks 16 and 18 having planar inner and outer surfaces 17A, 17B and 19A, 19B, respectively. Each of the disks 16, 18 includes an inner circumferential surface 21 that defines a central, circular aperture 20 centered about a center C of the disks 16, 18. Further referring to FIG. 2D, which shows a plan view of the disk 18, the surface 21 of each of the disks 16,18 is at a nominal radial distance R from the center C and includes a rectangularly-shaped notch 22 extending a maximum of a radial distance R8 away from the center C of the disks 16, 18.

Referring to FIGS. 2B, 2C and 2D, the disk 18 defines four apertures 26, which extend radially between a distance R1 and a distance R2 from the center C of the disk 18. Each of the apertures 26 is spaced about 90° from an adjacent aperture 26 and has a circumferential width W, except at rounded, opposing radial ends 27A and 27B. The radial end 27B extends inwardly toward the center C of the disk 18 starting from a radial distance R4 from the center C. The radial end 27A extends outwardly from the center C of the disk 18 starting from a radial distance R5 from the center C. In addition, the disk 18 defines an aperture 25 extending circumferentially between two of the apertures 26 and a radial distance of between R7 and R6 from the center C, where R7 is between R and R4 and R6 is slightly larger than R4.

Referring again to FIG. 2A and also to FIG. 2E, which is a top view of a circularly shaped coupling ring 33 which is part of the apparatus 30 used in the manufacture of the coil winding 15, and FIG. 2F, which is perspective view of the coupling ring 33, the coupling ring 33 includes an outer portion 34 encircling a portion of an outer circumferential surface 39 of a positioning ring connection portion 36. The outer portion 34 has a circumferential outer surface 35 at a radial distance R3 from a center C of the coupling ring 33 and a circumferential inner surface 37 at a radial distance R8 from the center C of the ring 33. The connection portion 36 includes an inner circumferential surface 41 defining an aperture 45 with a notch 46. The aperture 45 with the notch 46 has the same configuration and dimensions as the aperture 20 with the notch 22 of the disk 18. The portion of the surface 39 not encircled by the outer portion 34 includes three rectangularly shaped projections 43 having a maximum radial distance R3 from the center C and spaced about 90 degrees from each other. The notch 39 is spaced about 90 degrees from an adjacent projection 43.

Referring to FIG. 2A and to FIGS. 2G and 2H, which show plan and perspective views, respectively, of a circularly-shaped positioning ring 50 of the apparatus 30 used in the manufacture of the coil winding 15, the ring 50 includes inner and outer circumferential surfaces 52 and 54, respectively, and an inner circumferential surface 56. The inner surface 52 defines an aperture region 57 centered at a center C of the ring 50, is at a radial distance R3 from the center C of the ring 50 and has the same axial thickness as the surface 35 of the coupler ring 33. The inner surface 56 is at a nominal radial distance R8 from the center C and defines three apertures 58 having the same size and configuration, and positioned along the surface 56 in relation to one another in the same manner, as the projections 43 of the coupler ring 33. In addition, the outer surface 54 is at a nominal radial distance R4 from the center C, has an axial thickness T1 and defines four apertures 59. The apertures 59 extend radially toward the center C, are the same size and shape as the radial ends 27B of the ring 18 and have an axial thickness T2 that is less than the thickness T1.

Referring to FIGS. 2A-2H, the apparatus 30 is used to manufacture the coil winding 15, in accordance with the present invention, by inserting an end portion 60 of a flat copper wire 62, from the side 19A of the disk 18, through the aperture 25. The end portion 60 is then bent against the surface 19B of the disk 18, which secures the wire 62 for winding about the circumferential surface 54 of the ring 50 as described below. After the wire 62 is secured to the disk 18, the wire 62 is wound at least about one revolution around the surface 54. Then, after the center C of the ring 50 is aligned with the center C of the coupling ring 33 and the protrusions 43 are aligned with the apertures 58, the coupling ring 33 is inserted into the aperture 57, such that the protrusions 43 are received within the correspondingly aligned apertures 58, thereby mating the ring 50 to the coupling ring 33. Then, after the center C of the aperture 20 of the disk 16 is aligned with the centers C of the combination of the rings 33 and 50 and the center C of the aperture 20 of the disk 18, with the radial ends 27B of the disk 18 axially aligned with the apertures 59 in the ring 50, the surface 17A of the disk 16 is moved into contact with and forced against the outer radial surface of the ring 50 opposite the apertures 59, and the surface 19A of the disk 18 is moved into contact with and forced against the outer radial surface of the ring 50 defining the apertures 59. In the resulting combination, the disks 16 and 18 are aligned with each other and the ring 50 is disposed between the disks 16 and 18 and in a specific alignment with the disk 18.

While this aligned combination is maintained, a conventional, rotatable axle (not shown) having an outer circumferential surface with a notch of the same size and configuration as the aperture 20 with the notch 22 is inserted, threaded end first, through the aligned combination, such that the threaded end extends from the radial surface 19B. A securing means 70, such as a nut and bolt, is screwed onto the threaded end of the axle to fixedly secure the combination so that the disks 16 and 18 and the ring 50 cannot move axially relative to each other. The axle is then rotated, which causes the disks 16 and 18 with the ring 50 to rotate about the respective centers C. During rotation of the axle, the disks 16 and 18 accurately and precisely guide the wire 62 onto the surface 54 of the ring 50 as the wire 62 winds around the surface 54 and forms the coil winding 15 having a desired, predetermined axial and radial dimension. The number of times that the wire 62 is wound around the ring 50 is subject to the limitation that the outer surface of the outermost winding of the wire 62 does not exceed a radial distance R5 from the center C. Therefore, the coil winding 15 does not cover a portion of the aperture 26 at the radial distance of at least R5 from the center C, thereby providing that the coil winding 15 does not cover at least the end portion 27A at the furthest most radially extending portion of the aperture 26. In a preferred embodiment, the disks 16 and 18 are secured to the ring 50 and the ring 50 is precisely sized so that the dimension tolerance of the coil winding 15 in the direction axial to the winding of the wire 62 is within 0.2 mm of a predetermined, expected value, or at least within 1 mm of a predetermined, expected value, and further the axle is controllably rotated so that the radial dimension of the coil winding is within about 0.2 mm of a predetermined, expected value, or at least within about 1 mm of a predetermined, expected value.

After the wire 62 is wound around the ring 32 a desired number of times, a latch or fastener 80 is inserted into one of the apertures 26. Referring to FIG. 2I, which shows a perspective view of an exemplary fastener 80, which is preferably made of plastic, the fastener 80 includes ends 80A, 80B extending orthogonally from an interconnecting member 84 and including inner surfaces 86A, 86B, respectively, facing each other. The member 84 is fixed or adjustable in length, such that the distance between the inner surfaces 86A and 86 is fixed or adjustable in length. The end 80B is inserted through the end portion 27B of the aperture 26, and the end 80A is inserted through the portion of the aperture 26 not covered by the coil winding 15, which uncovered portion at least includes the end portion 27A. When the ends 80A, 80B of the fastener 80 are installed within the aperture 26, the end 86A faces and contacts the outermost winding of the coil winding 15 and the end 86B faces and contacts the innermost winding of the coil winding. The latch 52 is of a fixed length, or adjusted to a obtain a desired length, providing that the ends 86A, 86B force the outermost and innermost windings of the coil winding 15 toward each other so as to maintain a firm and tight winding of the wire 62, which substantially fixes the size and shape of the coil winding 15. Preferably, several latches 80 are installed in respective apertures 26 to fix the size and shape of the coil winding 15. After the latches 80 are installed, the securing means 70 is removed from the axle and the coil winding 15 wound around the ring 50 and including the attaches latches is separated from the coupling ring 33 and the disks 16 and 18. Advantageously, the ring 50 and the latches 80 of the apparatus 30, along with the disks 16 and 18, provide that the coil winding 15 manufactured by the apparatus 30 has a desired, predetermined shape and size, and that such manufacture provides a very high level of precision and is readily repeatable.

In the illustrated preferred embodiment, the latches 80 extend over only one radial surface or side of the coil winding 15. Consequently, the other side of the coil winding 15 can be positioned as close as possible to the outer surface 122 of the bottom portion 14 of the casing 12, which would be placed adjacent to or in contact with the head of a subject during operation of the TMS coil device 10. By placing the coil winding 15 in the casing 12 as close as possible to the surface 122, the stimulating power that will reach the subject's head is maximized.

In a further embodiment of the present invention, the manufacture of an induction coil winding for inclusion in the casing 12 of the TMS coil device 10 also includes encasing coil windings in a casting. Referring to FIG. 3, a mold 90 defining a casting region 92, and preferably including two alignment portions 94, is provided. In the illustrated embodiment, the casting region 92 is shaped to receive two induction coil windings 15, where each of the alignment portions 94 has a size and shape corresponding to the size and shape of the aperture 57 of the ring 50, and where each of the windings 15 is preferably manufactured as described above with a copper wire 62 wound around the positioning ring 50 and fixed in size and shape by latches 80. The manufacture of a single, integral casting 100 including the windings 15 is performed by disposing the rings 50 of the windings 15 adjacent to each other, with the apertures 57 respectively aligned with the portions 94, and then sliding the rings 50 over the respective portions 94 into the casting region 92. The portions 94 substantially fix the rings 50 and, thus each of the coil windings 15, in a predetermined location and orientation in relation to each other. After the coil windings 15 are fixedly positioned within the casting region 92, the casting region 92 is filled with casting material. When the casting material hardens, the casting 100 containing the two coil windings 15 wound around the respective rings 32 has been formed and is removed from the mold 90. The casting 100 ensures that the two coil windings 15 remain fixed in location and orientation in relation to each other, as provided by the portions 94.

In a further embodiment of the present invention, the manufacture of the TMS coil device includes coupling a pair of induction coil windings encased within a casting at a predetermined location within and orientation in relation to a casing having a predetermined size and shape. Referring to FIG. 4, the exemplary bottom portion 14 of the casing 12 of the TMS coil device 10 includes a side wall 110 and a bottom wall 112 defining a casting receiving region 114. The casting receiving region 114 has a predetermined size and shape and includes a pair of circularly-shaped protrusions 116 extending upwardly from the bottom wall 112. Each of the protrusions 116 has an outer diameter and height substantially equal to the inner diameter and axial thickness of the aperture 57 of the ring 50. Each of the protrusion 116 can receive and fixedly mate with the ring 50 of an induction coil winding 15, preferably which is substantially the same as the induction coil winding 15 with the fastener 80 and the ring 50 manufactured as described above, and most preferably, with the rings 50 of a casting 100 containing a pair of the coil windings 15 each with the fasteners 80 and the ring 50 manufactured as described above.

In one embodiment, the casting 100 containing the two coil windings 15 wound around the respective rings 50 is inserted into the region 114 by aligning the apertures 57 with the respective protrusions 116 and then sliding the rings 50 over the protrusions 116 until bottom surface 101 of the casting 100 contacts the opposing surface of the bottom wall 112. The protrusions 116, and optionally the side wall 110, with a high level of precision, fix the positioning rings 50, and thus the coil windings 15 contained in the casting 100, at a predetermined location within and orientation in relation to the bottom portion 14 of the casing 12. The casing 12 is closed by placing a top part covering (not shown) over the bottom portion 14. The top part covering has protrusions (not shown) opposite portions of the region 114 that, during installation of the casting 100 in the casing 12, force the positioning rings 50 firmly over the protrusions 116, such that the bottom surface 101 of the casting 100 contacts the opposing surface of the bottom wall 112 of the portion 14.

Thus, the bottom portion 14, and the positioning rings 50 around which the respective coil windings 15 are wound, accurately position the coil windings 15 in the direction axial to the coil windings 15, and preferably within about 0.1 mm of the expected location of the coil windings 15 in the bottom portion 14. In a further embodiment, the region 112 and the protrusions 116 are of a size and shape ensuring that the coil windings 15 or the casting material forming the casting 100 do not contact the wall 110 of the casing 12, and thus cause errors in the positioning of the coil windings 15 within the TMS coil device 10.

Advantageously, in accordance with the present invention, a coil winding can be manufactured precisely and repeatability to have a predetermined size and shape, and a coil winding can be positioned within a casing of a TMS coil device at a predetermined location and orientation in relation to another coil winding and the casing precisely and repeatably, where the casing has a predetermined Size and shape, such that information representative of the predetermined size and shape of the coil windings, and the location and orientation of the coil windings in relation to each other and the casing of the TMS coil device can be used to perform NBS with a high level of accuracy.

In a further preferred embodiment, the casting receiving region 114 is slightly larger in size than the casting 100 received and fixedly coupled within the casting region 114 of the casing 12. Referring to FIG. 4, and to FIG. 5A, which is a top view of an exemplary embodiment of the bottom portion 14 of the casing 12 including the casting 100 fixed within the region 114, and to FIG. 5B, which is cross-sectional view of the bottom portion 14 of FIG. 5A taken along cross-sectional line B-B, in accordance with the present invention, the casting region 114 is of a size and shape that a space 120 is defined between the bottom wall 112 and the side wall 110 and the portions of the casting 100 facing the walls 110 and 112. In a preferred embodiment, the side of the coil windings 15 opposite the side including the fasteners 80 constitutes the surface of the casting 100 facing the bottom wall 112 and defines the space 120 at least in part.

During manufacture of the casing 12, the bottom portion 14 is sealed with a gas contained in the space 120. The gas has a thermal conductivity lower than that of the coil windings 15 and the material from which the casing 12 is formed, so as to reduce the rate of transfer of heat energy from the coil windings 15 to the casing 12 during operation of the TMS coil, and where the thermal conductivity is not so low as to insulate the coil windings too much and cause the coil windings 15 to exceed a predetermined temperature too quickly during continuous or substantially continuous operation of the TMS coil device 10. The gas in the space 120 is preferably air. The thickness of the space 120, said thickness being the dimension extending between the bottom surface of the coil winding to the bottom wall of the casing, should not be greater than about 2 mm.

During operation of the TMS coil device 10, heat energy generated in the coil windings 15 radiates through the spacing 120 to the adjoining portions of the walls 110 and 112 of the casing 12. The transfer of a substantial amount of the heat energy generated at the coil winding 15 by radiation through the space 120, instead of by conduction through the casing material as existing in some prior art TMS coil devices, reduces the rate of transfer of the heat energy generated in the copper wire 62 of the coil windings 15 to the outer surface 122 of the casing 12 during operation of the TMS coil device 10. Although conduction of heat energy from the coil windings 15 to other portions of the casing 12 occurs through the positioning rings 50 and the casting material of the casting 100 surrounding the positioning rings 50, the spacing 120 substantially reduces the rate of transfer of heat energy to the surface 122 because a substantial portion of the heat energy generated at the coil windings 15, which otherwise would be transferred to the surface 122 from the facing surface of the coil windings 15, is instead radiated through the spacing 120. The spacing 120 with the gas causes heat energy to concentrate in the copper coil windings 15 and the casting material 100, thereby slowing transfer of the heat energy to the surface 122.

The spacing 120 in the TMS coil device 10, thus, reduces the rate at which heat energy from the coil windings 15 transfers to the surface 122, such that it takes a longer time period for the temperature of the outer surface 122 of the casing 12 to rise above a predetermined safety level. Consequently, a greater number of TMS pulses can be sequentially applied using the inventive device 10 before the temperature of the outer surface 122 exceed the predetermined safety level. For example, the advantages of the TMS coil device 10 with the spacing 120 are evident when its operability is compared to the operability of a similarly constructed TMS coil device which (i) does not have a space containing a gas, such as air, between a coil winding and the casing, or (ii) does not include a casting which encloses a coil winding and is separated from the casing by a spacing containing a gas, such as air. The TMS coil device 10 in accordance with the present invention can sequentially apply approximately double the number of TMS pulses than the comparable TMS coil devices without the spacing can apply before an unsafe temperature is reached at the outer surface of the TMS coil device 10.

As well known in the art, the temperature of a coil winding depends on the heating power, or the resistive losses in the copper wiring that forms the coil windings, and the mass and heat capacity of the material surrounding the copper wiring that absorbs the heat generated at the coil windings. In a further embodiment, referring to FIG. 1, a top wall 125 of the casing 12, which covers the side of the coil windings 15 opposite the bottom wall 122 of the casing 12, includes a phase transition material having a low conductivity, such as about 0.1-0.2 W/m*K, which transforms its phase from solid to liquid when heated, thereby increasing the heat capacity of the TMS coil device 10. In a further embodiment, the phase transition material is mixed with a binding material, so that the phase transition material changes its phase within the binding material, but the binding material remains solid. In another embodiment, the top wall 125 is formed from a material having good heat conductivity and electrical insulation properties, such as a ceramic solid structure or a powder of such material, to improve the transfer of heat energy from the coil windings 15 to the phase transition material in the top wall 125 of the casing 12.

Although preferred embodiments of the present invention have been described and illustrated, it will be apparent to those skilled in the art that various modifications may be made without departing from the principles of the invention.

What is claimed is:

1. A transcranial magnetic stimulation induction coil device comprising:
   at least one coil winding having a predetermined thickness and inner and outer surfaces at predetermined first and second radial lengths, respectively, from a center of the coil winding, wherein the first surface defines an aperture,
   a fastener extending from the inner surface of the coil winding to the outer surface of the coil winding, wherein the fastener couples the inner surface of the coil winding to the outer surface of the coil winding such that the coil winding has a predetermined size and shape, and
   a ring having an outer surface at a radial length from a center of the ring substantially equal to the first radial length, wherein the ring is positioned within the aperture of the coil winding such that the outer surface of the ring is in contact with the inner surface of the coil winding.

2. The device of claim 1, wherein the fastener includes a plastic material.

3. The device of claim 1, wherein the outer surface of the ring defines at least one notch extending radially toward the center of the ring, wherein the fastener has first and second ends, where the first end of the fastener is coupled to the inner surface of the coil winding at the notch and the second end of the fastener is coupled to the outer surface of the coil winding.

4. The device of claim 1 further comprising:
a casting of a predetermined size and shape encasing the coil winding at a predetermined location within, and orientation in relation to, the casting.

5. The device of claim 4 further comprising:
a casing having a predetermined size and shape and including a bottom wall and a side wall, wherein the bottom and side walls define a receiving region having a predetermined size and shape, wherein the casting is coupled to, and positioned at a predetermined location within and orientation in relation to, the receiving region.

6. The device of claim 5, wherein the bottom wall of the casing includes a projection extending into the receiving region at a predetermined location on the bottom wall, wherein the projection has a predetermined size and shape, wherein the casting defines an aperture at a predetermined location and having a predetermined size and shape matched to the predetermined size and shape of the projection in the casing, wherein the projection of the casing is mated to the aperture of the casting such that the coil winding within the casing is at a predetermined location within and orientation in relation to the casing.

7. The device of claim 6, wherein the casting includes a bottom outer surface facing the bottom wall of the casing, wherein at least a portion of the bottom wall of the casing and at least a portion of the bottom outer surface of the casting define a space there between, and wherein the space includes a gas.

8. The device of claim 7, wherein the gas includes air.

9. The device of claim 7, wherein the coil winding has a bottom surface facing the bottom wall of the casing and constituting a portion of the bottom outer surface of the casing, wherein the bottom surface of the coil winding defines a portion of the space, wherein the space has a thickness dimension extending between the bottom surface of the coil winding and the bottom wall of casing, and wherein the thickness dimension is not greater than about 2 mm.

10. The device of claim 7, wherein the casing includes a top wall overlying a side of the coil winding opposite to the bottom wall of the casing, and wherein the top wall includes a phase transition material having a heat conductivity substantially lower than the conductivity of ceramic.

11. The device of claim 1 further comprising:
a casing having a predetermined size and shape and including a bottom wall and a side wall, wherein the bottom and side walls define a receiving region having a predetermined size and shape, wherein the coil winding is coupled to, and positioned at a predetermined location within and orientation in relation to, the receiving region.

12. The device of claim 11, wherein the coil winding includes a bottom outer surface facing the bottom wall of the casing, wherein at least a portion of the bottom outer surface of the coil winding and at least a portion of the bottom outer surface of the casing define a space there between, and wherein the space includes a gas.

13. The device of claim 1 further comprising;
at least one additional coil winding having a predetermined thickness and inner and outer surfaces at predetermined first and second radial lengths substantially equal to the those of the first coil, respectively, from a center of the coil winding, wherein the first surface defines an aperture,
a fastener extending from the inner surface of the coil winding to the outer surface of the coil winding, wherein the fastener couples the inner surface of the coil winding to the outer surface of the coil winding such that the coil winding has a predetermined size and shape, and
a ring having an outer surface at a radial length from a center of the ring substantially equal to the first radial length, wherein the ring is positioned within the aperture of the coil winding such that the outer surface of the ring is in contact with the inner surface of the coil winding.

14. The device of claim 13 further comprising:
a casting of a predetermined size and shape encasing the coil windings at a predetermined location within, and orientation in relation to, the casting.

15. The device of claim 13, wherein the fasteners are only on one side of the coil winding.

\* \* \* \* \*